(12) United States Patent
Nita et al.

(10) Patent No.: US 10,130,380 B2
(45) Date of Patent: Nov. 20, 2018

(54) ULTRASOUND CATHETER APPARATUS

(71) Applicant: Bard Peripheral Vascular, Inc., Tempe, AZ (US)

(72) Inventors: Henry Nita, Redwood City, CA (US); Jeff Sarge, Fremont, CA (US); Simon Nguyen, San Jose, CA (US)

(73) Assignee: Flowcardia, Inc., Tempe, AZ (US)

( * ) Notice: Subject to any disclaimer, the term of this patent is extended or adjusted under 35 U.S.C. 154(b) by 0 days.

(21) Appl. No.: 14/616,601

(22) Filed: Feb. 6, 2015

(65) Prior Publication Data

US 2015/0150571 A1  Jun. 4, 2015

Related U.S. Application Data

(60) Continuation of application No. 12/572,118, filed on Oct. 1, 2009, now Pat. No. 8,961,423, which is a
(Continued)

(51) Int. Cl.
*A61B 17/22* (2006.01)
*A61B 17/00* (2006.01)

(52) U.S. Cl.
CPC ............ *A61B 17/22012* (2013.01); *A61B 2017/00477* (2013.01); *A61B 2017/22015* (2013.01)

(58) Field of Classification Search
CPC ........... A61B 2017/22015; A61B 2017/00477; A61B 2017/22012; A61B 8/4281;
(Continued)

(56) References Cited

U.S. PATENT DOCUMENTS 3,296,620 A  1/1967 Rodda
3,433,226 A  3/1969 Boyd
(Continued)

FOREIGN PATENT DOCUMENTS

AU  2007240154 A1  1/2008
DE  2256127 A1  5/1974
(Continued)

OTHER PUBLICATIONS

Noone, D.: Experimental and Numerical Investigation of Wire Waveguides for Therapeutic Ultrasound Angioplasty. M.Eng. Dublin City University. 2008.
(Continued)

*Primary Examiner* — Christopher L Templeton
*Assistant Examiner* — Mikail Mannan

(57) ABSTRACT

Ultrasound catheter devices and methods of the present invention generally provide for ablation and/or disruption of vascular occlusions. An ultrasound transmission member, such as a wire, transmits vibrational energy from an ultrasound transducer to a distal head of the catheter to disrupt vascular occlusions. An absorber member is disposed on or around the ultrasound transmission wire at a location adjacent the sonic connector of the catheter. The absorber member absorbs heat, vibrations, and/or the like from the ultrasound transmission wire at or near the area where the transmission wire is coupled with the sonic connector. The absorptive function typically slows the process of wear and tear on the transmission wire, thus extending the useful life of the ultrasound catheter.

19 Claims, 5 Drawing Sheets

Related U.S. Application Data continuation of application No. 11/179,829, filed on Jul. 11, 2005, now Pat. No. 7,621,929, which is a division of application No. 10/375,903, filed on Feb. 26, 2003, now Pat. No. 6,942,677.

(58) Field of Classification Search
CPC ... A61B 8/12; A61B 8/4461; A61B 17/22004; A61B 17/22012; A61B 17/2202; A61B 2017/22027; A61B 2017/22014
See application file for complete search history.

(56) References Cited

U.S. PATENT DOCUMENTS

| | | | |
|---|---|---|---|
| 3,443,226 A | 5/1969 | Knight | |
| 3,565,062 A | 2/1971 | Kurls | |
| 3,585,082 A | 6/1971 | Siller | |
| 3,612,038 A | 10/1971 | Halligan | |
| 3,631,848 A | 1/1972 | Muller | |
| 3,679,378 A | 7/1972 | Van Impe et al. | |
| 3,719,737 A | 3/1973 | Vaillancourt et al. | |
| 3,739,460 A | 6/1973 | Addis et al. | |
| 3,754,746 A * | 8/1973 | Thiele | F16F 7/12 188/268 |
| 3,823,717 A | 7/1974 | Pohlman et al. | |
| 3,835,690 A | 9/1974 | Leonhardt et al. | |
| 3,839,841 A | 10/1974 | Amplatz | |
| 3,896,811 A | 7/1975 | Storz | |
| 4,016,882 A | 4/1977 | Broadwin et al. | |
| 4,033,331 A | 7/1977 | Guss et al. | |
| 4,136,700 A | 1/1979 | Broadwin et al. | |
| 4,337,090 A | 6/1982 | Harrison | |
| 4,368,410 A | 1/1983 | Hance et al. | |
| 4,417,578 A | 11/1983 | Banko | |
| 4,425,115 A | 1/1984 | Wuchinich | |
| 4,486,680 A | 12/1984 | Bonnet et al. | |
| 4,505,767 A | 3/1985 | Quin | |
| 4,545,767 A | 10/1985 | Suzuki et al. | |
| 4,565,589 A | 1/1986 | Harrison | |
| 4,565,787 A | 1/1986 | Bossle et al. | |
| 4,572,184 A | 2/1986 | Stohl et al. | |
| 4,664,112 A | 5/1987 | Kensey et al. | |
| 4,665,906 A | 5/1987 | Jervis | |
| 4,679,558 A | 7/1987 | Kensey et al. | |
| 4,700,705 A | 10/1987 | Kensey et al. | |
| 4,721,117 A | 1/1988 | Mar et al. | |
| 4,750,902 A | 6/1988 | Wuchinich et al. | |
| 4,808,153 A | 2/1989 | Parisi | |
| 4,811,743 A | 3/1989 | Stevens | |
| 4,827,911 A | 5/1989 | Broadwin et al. | |
| 4,838,853 A | 6/1989 | Parisi | |
| 4,854,325 A | 8/1989 | Stevens | |
| 4,870,953 A | 10/1989 | DonMicheal et al. | |
| 4,886,060 A | 12/1989 | Wiksell | |
| 4,920,954 A | 5/1990 | Alliger et al. | |
| 4,923,462 A | 5/1990 | Stevens | |
| 4,924,863 A | 5/1990 | Sterzer | |
| 4,931,047 A | 6/1990 | Broadwin et al. | |
| 4,936,281 A | 6/1990 | Stasz | |
| 4,936,845 A | 6/1990 | Stevens | |
| 5,000,185 A | 3/1991 | Yock | |
| 5,015,227 A | 5/1991 | Broadwin et al. | |
| 5,026,384 A | 6/1991 | Farr et al. | |
| 5,030,357 A | 7/1991 | Lowe | |
| 5,046,503 A | 9/1991 | Schneiderman | |
| 5,053,008 A | 10/1991 | Bajaj | |
| 5,058,570 A | 10/1991 | Idemoto et al. | |
| 5,076,276 A | 12/1991 | Sakurai et al. | |
| 5,091,205 A | 2/1992 | Fan | |
| 5,100,423 A | 3/1992 | Fearnot | |
| 5,109,859 A | 5/1992 | Jenkins | |
| 5,114,414 A | 5/1992 | Buchbinder | |
| 5,116,350 A | 5/1992 | Stevens | |
| 5,127,917 A | 7/1992 | Niederhauser et al. | |
| 5,156,143 A | 10/1992 | Bocquet et al. | |
| 5,163,421 A | 11/1992 | Bernstein et al. | |
| 5,171,216 A | 12/1992 | Dasse et al. | |
| 5,180,363 A | 1/1993 | Idemoto et al. | |
| 5,183,470 A | 2/1993 | Wettermann | |
| 5,195,955 A | 3/1993 | Don Michael | |
| 5,215,614 A | 6/1993 | Wijkamp et al. | |
| 5,217,565 A | 6/1993 | Kou et al. | |
| 5,221,255 A | 6/1993 | Mahurkar et al. | |
| 5,226,421 A | 7/1993 | Frisbie et al. | |
| 5,234,416 A | 8/1993 | Macaulay et al. | |
| 5,238,004 A | 8/1993 | Sahatjian et al. | |
| 5,242,385 A | 9/1993 | Strukel | |
| 5,243,997 A | 9/1993 | Uflacker et al. | |
| 5,248,296 A | 9/1993 | Alliger | |
| 5,255,669 A | 10/1993 | Kubota et al. | |
| 5,267,954 A | 12/1993 | Nita | |
| 5,269,291 A | 12/1993 | Carter | |
| 5,269,297 A | 12/1993 | Weng et al. | |
| 5,269,793 A | 12/1993 | Simpson | |
| 5,287,858 A | 2/1994 | Hammerslag et al. | |
| 5,290,229 A | 3/1994 | Paskar | |
| 5,304,115 A | 4/1994 | Pflueger et al. | |
| 5,304,131 A | 4/1994 | Paskar | |
| 5,312,328 A * | 5/1994 | Nita | A61B 17/22012 604/22 |
| 5,318,014 A | 6/1994 | Carter | |
| 5,318,570 A | 6/1994 | Hood et al. | |
| 5,324,255 A | 6/1994 | Passafaro et al. | |
| 5,324,260 A | 6/1994 | O'Neill et al. | |
| 5,325,860 A | 7/1994 | Seward et al. | |
| 5,326,342 A | 7/1994 | Pflueger et al. | |
| 5,328,004 A | 7/1994 | Fannin et al. | |
| 5,329,927 A | 7/1994 | Gardineer et al. | |
| 5,341,818 A | 8/1994 | Abrams et al. | |
| 5,342,292 A | 8/1994 | Nita et al. | |
| 5,344,395 A | 9/1994 | Whalen et al. | |
| 5,346,502 A | 9/1994 | Estabrook et al. | |
| 5,362,309 A | 11/1994 | Carter | |
| 5,368,557 A | 11/1994 | Nita | |
| 5,368,558 A | 11/1994 | Nita et al. | |
| 5,376,084 A | 12/1994 | Bacich et al. | |
| 5,378,234 A | 1/1995 | Hammerslag et al. | |
| 5,380,274 A | 1/1995 | Nita | |
| 5,380,316 A | 1/1995 | Aita et al. | |
| 5,382,228 A * | 1/1995 | Nita | A61B 17/22012 601/3 |
| 5,383,460 A | 1/1995 | Jang et al. | |
| 5,389,096 A | 2/1995 | Aita et al. | |
| 5,391,144 A | 2/1995 | Sakurai et al. | |
| 5,397,293 A | 3/1995 | Alliger et al. | |
| 5,397,301 A | 3/1995 | Pflueger et al. | |
| 5,405,318 A | 4/1995 | Nita | |
| 5,409,483 A | 4/1995 | Campbell et al. | |
| 5,417,672 A | 5/1995 | Nita et al. | |
| 5,417,703 A | 5/1995 | Brown et al. | |
| 5,421,923 A | 6/1995 | Clarke et al. | |
| 5,427,118 A | 6/1995 | Nita et al. | |
| 5,431,168 A | 7/1995 | Webster, Jr. | |
| 5,431,663 A | 7/1995 | Carter | |
| 5,443,078 A | 8/1995 | Uflacker | |
| 5,447,509 A | 9/1995 | Mills et al. | |
| 5,449,369 A | 9/1995 | Imran | |
| 5,451,209 A | 9/1995 | Ainsworth et al. | |
| 5,465,733 A | 11/1995 | Hinohara et al. | |
| 5,474,531 A | 12/1995 | Carter | |
| 5,480,379 A | 1/1996 | La Rosa | |
| 5,484,398 A | 1/1996 | Stoddard | |
| 5,487,757 A | 1/1996 | Truckai et al. | |
| 5,507,738 A | 4/1996 | Ciervo | |
| 5,516,043 A | 5/1996 | Manna et al. | |
| 5,527,273 A | 6/1996 | Manna et al. | |
| 5,540,656 A | 7/1996 | Pflueger et al. | |
| 5,542,917 A | 8/1996 | Nita et al. | |
| 5,597,497 A | 1/1997 | Dean et al. | |
| 5,597,882 A | 1/1997 | Schiller et al. | |
| 5,607,421 A | 3/1997 | Jeevanandam et al. | |
| 5,611,807 A | 3/1997 | O'Boyle | |
| 5,618,266 A | 4/1997 | Liprie | |
| 5,626,593 A | 5/1997 | Imran | |

(56) References Cited

U.S. PATENT DOCUMENTS

| | | |
|---|---|---|
| 5,627,365 A | 5/1997 | Chiba et al. |
| 5,649,935 A | 7/1997 | Kremer et al. |
| 5,658,282 A | 8/1997 | Daw et al. |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,222 A | 11/1998 | Makower |
| 5,846,218 A | 12/1998 | Brisken et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,913,192 A | 6/1999 | Parthasarathy et al. |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,007,499 A | 12/1999 | Martin et al. |
| 6,007,514 A | 12/1999 | Nita |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,051,010 A | 4/2000 | DiMatteo et al. |
| 6,113,558 A | 9/2000 | Rosenschein et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth et al. |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |

(56) References Cited

U.S. PATENT DOCUMENTS

| | | |
|---|---|---|
| 7,137,963 B2 | 11/2006 | Nita et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,771,358 B2 | 8/2010 | Moehring et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,935,108 B2 | 5/2011 | Baxter et al. |
| 7,938,819 B2 | 5/2011 | Kugler et al. |
| 7,955,293 B2 | 6/2011 | Nita et al. |
| 8,043,251 B2 | 10/2011 | Nita et al. |
| 8,083,727 B2 | 12/2011 | Kugler et al. |
| 8,133,236 B2 | 3/2012 | Nita |
| 8,221,343 B2 | 7/2012 | Nita et al. |
| 8,226,566 B2 | 7/2012 | Nita |
| 8,246,643 B2 | 8/2012 | Nita |
| 8,308,677 B2 | 11/2012 | Nita et al. |
| 8,506,519 B2 | 8/2013 | Nita |
| 8,617,096 B2 | 12/2013 | Nita et al. |
| 8,632,560 B2 | 1/2014 | Pal et al. |
| 8,647,296 B2 | 2/2014 | Moberg et al. |
| 8,690,819 B2 | 4/2014 | Nita et al. |
| 8,790,291 B2 | 7/2014 | Nita et al. |
| 8,974,446 B2 | 3/2015 | Nguyen et al. |
| 9,107,590 B2 | 8/2015 | Hansmann et al. |
| 9,265,520 B2 | 2/2016 | Nita |
| 9,282,984 B2 | 3/2016 | Nita |
| 9,314,258 B2 | 4/2016 | Nita et al. |
| 9,770,250 B2 | 9/2017 | Nita et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0024393 A1 | 2/2004 | Nita et al. |
| 2005/0033311 A1 | 2/2005 | Guldfeldt et al. |
| 2005/0228286 A1 | 10/2005 | Messerly et al. |
| 2006/0206039 A1 | 9/2006 | Wilson et al. |
| 2006/0264809 A1 | 11/2006 | Hansmann et al. |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2010/0023037 A1 | 1/2010 | Nita et al. |
| 2011/0105960 A1 | 5/2011 | Wallace |
| 2011/0130834 A1 | 6/2011 | Wilson et al. |
| 2011/0237982 A1 | 9/2011 | Wallace |
| 2011/0313328 A1 | 12/2011 | Nita |
| 2012/0130475 A1 | 5/2012 | Shaw |
| 2012/0311844 A1 | 12/2012 | Nita et al. |
| 2012/0330196 A1 | 12/2012 | Nita |
| 2014/0081288 A1 | 3/2014 | Nita et al. |
| 2014/0243712 A1 | 8/2014 | Humayun et al. |
| 2015/0190660 A1 | 7/2015 | Sarge et al. |
| 2015/0359651 A1 | 12/2015 | Wübbeling |
| 2016/0128717 A1 | 5/2016 | Nita |
| 2016/0183956 A1 | 6/2016 | Nita |
| 2016/0271362 A1 | 9/2016 | Van Liere |
| 2017/0354428 A1 | 12/2017 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0541249 A2 | 5/1993 |
| EP | 0820728 A2 | 1/1998 |
| EP | 1323481 A2 | 7/2003 |
| GB | 1106957 | 3/1968 |
| JP | 61-272045 A | 12/1986 |
| JP | H2-7150 U | 10/1988 |
| JP | 01-099547 | 4/1989 |
| JP | 3-67608 U | 7/1991 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 0053341 A1 | 9/2000 |
| WO | 0067830 A1 | 11/2000 |
| WO | 03039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2006049593 A1 | 5/2006 |
| WO | 2014022716 A2 | 2/2014 |

OTHER PUBLICATIONS

Definition of the term "connected", retrieved on Sep. 21, 2013. <www.thefreedictionary.com/connected> 1 page total.

Supplemental European Search Report dated Nov. 5, 2009 for European Application No. EP03766931.

International Search Report dated Oct. 28, 2003 for PCT Application No. PCT/US2003/023468.

Extended European Search Report dated Mar. 22, 2012 for European Application No. EP11188799.

International Search Report dated Dec. 23, 2005 for PCT Application No. PCT/US2004/019378.

(56) References Cited

OTHER PUBLICATIONS

Extended European Search Report for Patent Application No. 06718204.8, dated May 30, 2012.
International Search Report dated Aug. 1, 2013 for PCT Application No. PCT/US2013/053306.
International Preliminary Report dated Aug. 1, 2013 for PCT Application No. PCT/US2013/053306.
Written Opinion dated Aug. 1, 2013 for PCT Application No. PCT/US2013/053306.
Supplemental European Search Report dated Apr. 29, 2009 for European Application No. EP 04711207.3.
Calhoun et al., "Electron-Beam Systems for Medical Device Sterilization", downloaded from web on Oct. 8, 2002 <http://www.devicelink.com/mpb/archive/97/07/002.html> 7 pages total.
Definition of the term "coupled", retrieved on May 18, 2013. <http://www.merriam-webster.com/dictionary/couple> 1 page total.
"E-Beam Theory" RDI-IBA Technology Group, downloaded from web on Oct. 8, 2002 <http://www.e-beamrdi/EbeamTheory.htm> 2 pages total.
Japanese Office Action for Japanese Application No. 2010-134566, dated Mar. 2, 2012.
Sehgal, et al., Ultrasound-Assisted Thrombolysis, Investigative Radiology, 1993, vol. 28, Issue 10, pp. 939-943.
Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002, 4 pages total. <http://www.ms.oml.gov/researchgroups/composites/new%20orccmt%20pages/pages/ebwha>.
Extended European Search Report dated Mar. 5, 2012 for European Application No. 12153606.4-1269.
Margaret Fyfe et al., Mast cell degranulation and increased vascular permeability induced by therapeutic' ultrasound in the rate ankle joint, Br. J. exp. Path., 1984, vol. 65, pp. 671-676.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.

\* cited by examiner

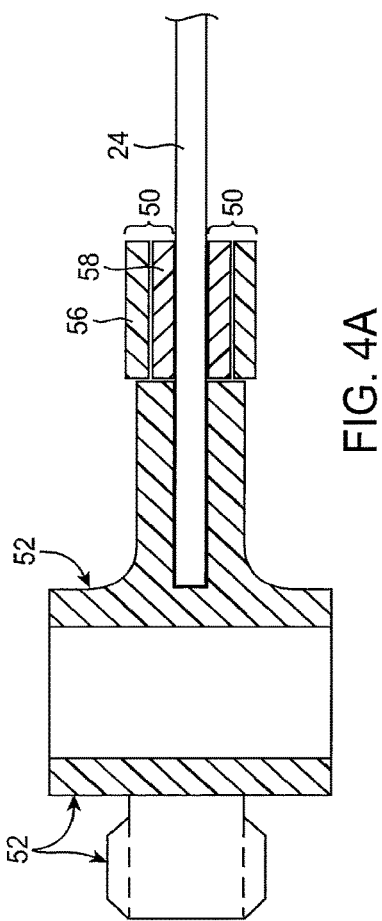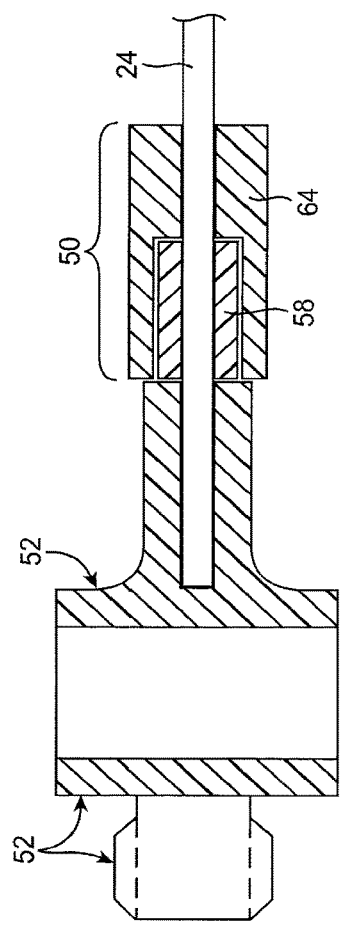

ULTRASOUND CATHETER APPARATUS

This application is a continuation of U.S. patent application Ser. No. 12/572,118, filed Oct. 1, 2009, issued as U.S. Pat. No. 8,961,423, which is a continuation of U.S. patent application Ser. No. 11/179,829, filed Jul. 11, 2005, issued as U.S. Pat. No. 7,621,929, which is a division of U.S. patent application Ser. No. 10/375,903, filed Feb. 26, 2003, issued as U.S. Pat. No. 6,942,677, and is related to U.S. patent application Ser. No. 10/229,371, filed Aug. 26, 2002, which issued as U.S. Pat. No. 7,137,963, the full disclosures of which are hereby incorporated by reference.

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), U.S. Pat. No. 4,870,953 (Don Michael, et al), and U.S. Pat. No. 4,920,954 (Alliger, et al.), as well as other patent publications W087-05739 (Cooper), W089-06515 (Bernstein, et al.), W090-0130 (Sonic Needle Corp.), EP, EP316789 (Don Michael, et al.), DE3,821,836 (Schubert) and DE2438648 (Pohlman). While many ultrasound catheters have been developed, however, improvements are still being pursued.

Typically, an ultrasonic catheter system for ablating occlusive material includes three basic components: an ultrasound generator, an ultrasound transducer, and an ultrasound catheter. The generator converts line power into a high frequency current that is delivered to the transducer. The transducer contains piezoelectric crystals which, when excited by the high frequency current, expand and contract at high frequency. These small, high-frequency expansions and contractions have both longitudinal and transverse components (relative to an axis of the transducer and the catheter), which are amplified by the transducer horn into vibrational energy. The vibrations are then transmitted from the transducer through the ultrasound catheter via an ultrasound transmission member (or wire) running longitudinally through the catheter. The transmission member transmits the vibrational energy to the distal end of the catheter where the energy is used to ablate or otherwise disrupt a vascular obstruction.

To effectively reach various sites for treatment of intravascular occlusions, ultrasound catheters of the type described above typically have lengths of about 150 cm or longer. To permit the advancement of such ultrasound catheters through small and/or tortuous blood vessels such as the aortic arch, coronary vessels, and peripheral vasculature of the lower extremities, the catheters (and their respective ultrasound transmission wires) must typically be sufficiently small and flexible. Due to attenuation of ultrasound energy along the long, thin, ultrasound transmission wire, a sufficient amount of vibrational energy must be applied at the proximal end of the wire to provide a desired amount of energy at the distal end.

An ultrasound transmission wire is usually coupled at its proximal end with the transducer by means of a sonic connector. The sonic connector typically has a significantly larger diameter than that of the ultrasound transmission member, the difference in diameters helping to amplify the vibrational energy being transmitted from the transducer to the transmission wire. This amplification of vibrations, however, creates stress and heat in the transmission wire in an area adjacent its connection with the sonic connector. Stress and heat generated by these amplified vibrations (especially transverse vibrations) significantly reduce the usable life of the ultrasound transmission wire and may cause its premature breakage at or near the point of contact with the sonic connector.

Efforts have been made to reduce transverse vibrations somewhere along the length of an ultrasound transmission member. For example, U.S. Pat. Nos. 5,382,228 and 6,494,891, both of which issued to an inventor of the present invention and are hereby incorporated by reference, describe mechanisms for absorbing transverse motion of an ultrasound transmission wire. Currently available devices and devices described in the above patents, however, to not reduce stress and/or heat in an ultrasound transmission wire at or near its point of contact with a sonic connector as much as may be desired. As just discussed, this proximal area of the transmission wire may be one of the most vulnerable areas due to its exposure to amplified vibrational energy from the sonic connector.

Therefore, a need exists for an improved ultrasound catheter device and method that provides ablation or disruption of vascular occlusions. Ideally, the ultrasound catheter would include means for reducing heat in the ultrasound transmission wire component of the catheter at or near its coupling with the sonic connector component. Alternatively or additionally, it would also be ideal if transverse vibrations and stress were reduced in a proximal portion of the transmission wire. Such catheter devices would ideally be sufficiently thin and flexible to be advanced through narrow, tortuous vasculature, such as the coronary vasculature, while also being configured to enhance the usable life of the ultrasound transmission wire. At least some of these objectives will be met by the present invention.

BRIEF SUMMARY OF THE INVENTION

Ultrasound catheter devices and methods of the present invention generally provide for ablation and/or disruption of vascular occlusions. An ultrasound transmission member, such as a wire, transmits vibrational energy from an ultrasound transducer to a distal head of the catheter to disrupt vascular occlusions. At least one absorber member is disposed on or around the ultrasound transmission wire at a location adjacent the sonic connector of the catheter. The absorber member absorbs heat, vibrations, and/or the like from the ultrasound transmission wire at or near the area where the transmission wire is coupled with the sonic connector. The absorptive function typically slows the process of wear and tear on the transmission wire, thus extending the useful life of the ultrasound catheter.

In one aspect of the invention, an ultrasound catheter for disrupting occlusions in blood vessels comprises: an elongate flexible catheter body having a proximal end, a distal end and at least one lumen; an ultrasound transmission member extending longitudinally through the lumen of the catheter body; a sonic connector coupled with a proximal end of the ultrasound transmission member for coupling the ultrasound transmission member with a separate ultrasound generating device; and at least one heat absorbing member coupled with the ultrasound transmission member adjacent the sonic connector. In some embodiments, the heat absorbing member surrounds a portion of the ultrasound transmission member adjacent a distal end of the sonic connector. Optionally, the heat absorbing member includes a bore for receiving the ultrasound transmission member. In some embodiments, such a heat absorbing member is tubular.

In some embodiments, the heat absorbing member contacts a distal end of the sonic connector, while in other embodiments the heat absorbing member may be separated from a distal end of the sonic connector by a distance of a few millimeters. The heat absorbing member may comprise one piece or, in other embodiments, the heat absorbing member may comprise at least two component parts such as at least one absorptive part in contact with the transmission member for absorbing heat and at least one constraining part coupled with the absorptive part for holding the absorptive part in place on the transmission member. In some such embodiments, the constraining part contacts the transmission member and comprises at least one absorptive material for absorbing heat. In various embodiments, the constraining part may either contact a portion of the sonic connector or overlap a portion of the sonic connector. Optionally, at least one of the absorptive part and the constraining part may be capable of absorbing vibrations. In some embodiments, the constraining part comprises a bore for receiving the ultrasound transmission wire, wherein the bore includes a widened portion for receiving the absorptive part. In some embodiments, the constraining part is tubular. Also in some embodiments, the constraining part is coupled with at least one of the absorptive part and the ultrasound transmission wire by at least one of crimping, bonding, fusing or welding.

In other embodiments, the heat absorbing member comprises at least two component parts comprising at least one vibration absorptive part in contact with the transmission member for absorbing vibrations and at least one constraining part coupled with the absorptive part for holding the absorptive part in place on the transmission member and for absorbing heat. In some embodiments, the constraining part contacts a portion of the sonic connector, while in other embodiments it overlaps a portion of the sonic connector. In some embodiments, the constraining part comprises a bore for receiving the ultrasound transmission wire, wherein the bore includes a widened portion for receiving the absorptive part. In such embodiments, the constraining part may sometimes be tubular.

In some embodiments, the heat absorbing member is capable of absorbing vibrations. In other embodiments, the ultrasound catheter further includes a vibrational absorbing member coupled with the ultrasound transmission member for absorbing vibrations. In either case, the heat absorbing member may comprise at least one metal having heat conductivity properties. The metal(s) may include, but are not limited to, aluminum and its alloys, titanium and its alloys, and/or magnesium and its alloys. Finally, in some embodiments the heat absorbing member is coupled with the ultrasound transmission wire by at least one of crimping, bonding, fusing or welding.

In another aspect, an ultrasound catheter for disrupting occlusions in blood vessels includes: an elongate flexible catheter body having a proximal end, a distal end and at least one lumen; an ultrasound transmission member extending longitudinally through the lumen of the catheter body; a sonic connector coupled with a proximal end of the ultrasound transmission member for coupling the ultrasound transmission member with a separate ultrasound generating device; and at least one vibration absorbing member coupled with the ultrasound transmission member adjacent the sonic connector. Any of the features and combinations described for the embodiments above may be equally applied to this aspect of the invention.

In some embodiments, the vibration absorbing member surrounds a portion of the ultrasound transmission member adjacent a distal end of the sonic connector. For example, the vibration absorbing member may include a bore for receiving the ultrasound transmission member. In some embodiments, the vibration absorbing member is tubular. In some embodiments, the vibration absorbing member contacts a distal end of the sonic connector, while in others it is separated from a distal end of the sonic connector by a distance of a few millimeters. For example, in some embodiments, the absorbing member may be separated from the sonic connector by approximately ¼ of a wavelength produced by the ultrasound device.

In some embodiments, the vibration absorbing member comprises at least two component parts, the component parts comprising: at least one absorptive part in contact with the transmission member for absorbing vibrations; and at least one constraining part coupled with the absorptive part for holding the absorptive part in place on the transmission member. In some embodiments, the at least one constraining part contacts the transmission member and comprises at least one absorptive material for absorbing heat. Also in some embodiments, the at least one constraining part contacts or overlaps a portion of the sonic connector. In some embodiments, at least one of the absorptive part and the constraining part is capable of absorbing heat. In some embodiments, the at least one constraining part comprises a bore for receiving the ultrasound transmission wire, wherein the bore includes a widened portion for receiving the absorptive part. In such embodiments, the constraining part may be tubular. The constraining part may be coupled with at least one of the absorptive part and the ultrasound transmission wire by at least one of crimping, bonding, fusing or welding.

In other embodiments, the vibration absorbing member comprises at least two component parts, the component parts comprising: at least one vibration absorptive part in contact with the transmission member for absorbing vibrations; and at least one constraining part coupled with the absorptive part for holding the absorptive part in place on the transmission member and for absorbing heat. The at least one constraining part may contact or overlap a portion of the sonic connector in various embodiments. Optionally, the constraining part may include a bore for receiving the ultrasound transmission wire, wherein the bore includes a widened portion for receiving the absorptive part. In such embodiments, the constraining part may be tubular, for example.

In some embodiments, the vibration absorbing member is capable of absorbing heat. In other embodiments, the ultrasound catheter further includes a heat absorbing member coupled with the ultrasound transmission member for absorbing heat. In some embodiments the vibration absorbing member comprises at least one vibration absorbing material selected from the group consisting of rubbers and polymers. In some embodiments, the vibration absorbing member further comprises at least one metal having heat conductivity properties. For example, such a metal may be selected from the group consisting of aluminum, titanium, and magnesium. In some embodiments, the vibration absorbing member is coupled with the ultrasound transmission wire by at least one of crimping, bonding, fusing or welding.

BRIEF DESCRIPTION OF THE DRAWINGS

FIGS. 4A-4C are cross-sectional views of proximal ends of ultrasound catheters having absorber members according to various embodiments of the invention.

DETAILED DESCRIPTION OF THE INVENTION

Ultrasound catheter devices and methods of the present invention generally provide for ablation and/or disruption of vascular occlusions. An ultrasound transmission member, such as a wire, transmits vibrational energy from an ultrasound transducer to a distal head of the catheter to disrupt vascular occlusions. At least one absorber member is disposed on or around the ultrasound transmission wire at a location adjacent the sonic connector of the catheter. The absorber member absorbs heat, vibrations, and/or the like from the ultrasound transmission wire at or near the area where the transmission wire is coupled with the sonic connector. The absorptive function typically slows the process of wear and tear on the transmission wire, thus extending the useful life of the ultrasound catheter. Although catheters of the invention are described in detail below, for further details reference may be made to U.S. patent application Ser. No. 10/229,371, filed Aug. 26, 2002, which was previously incorporated by reference.

Figure 1:
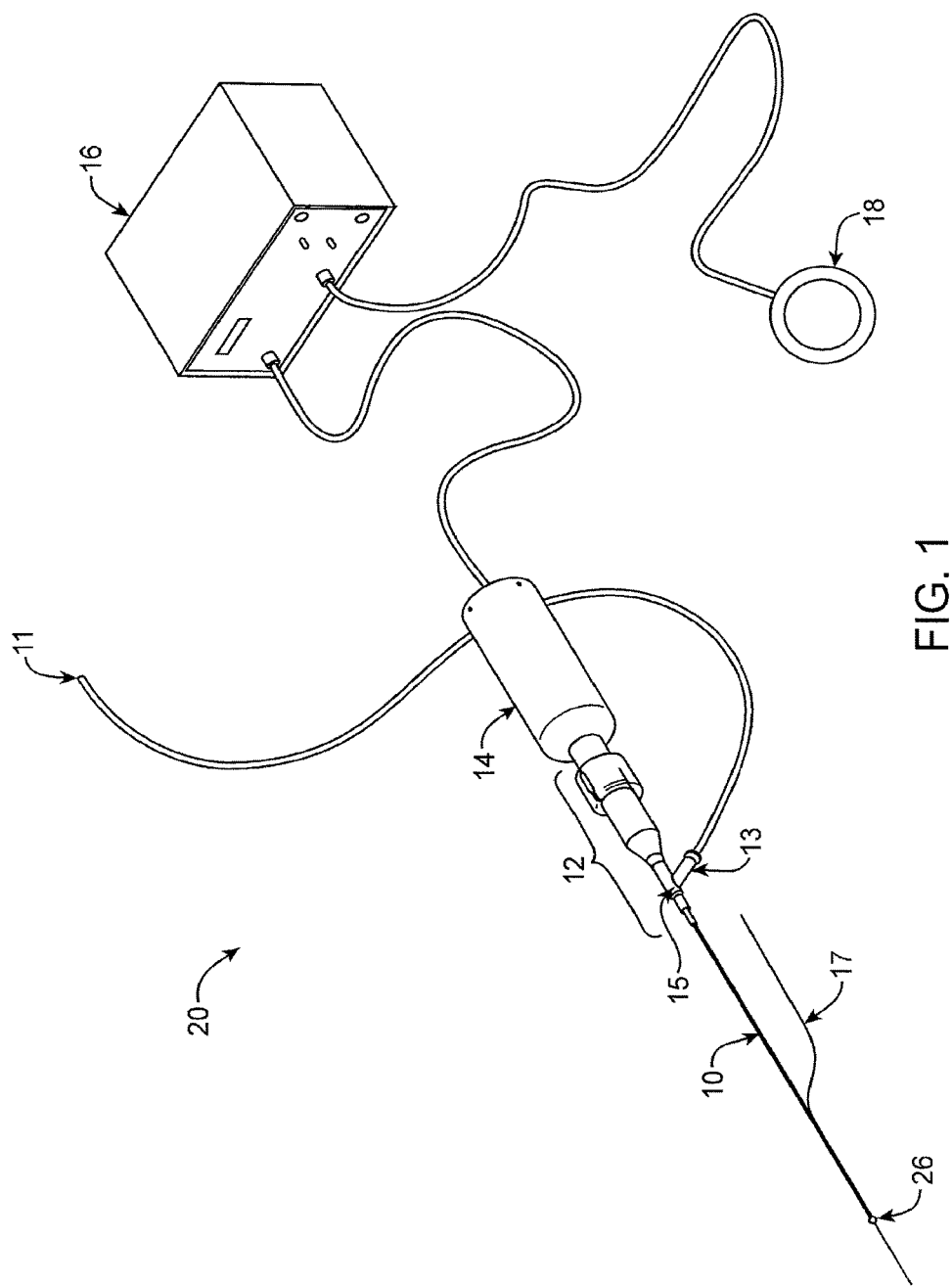
FIG. 1 is a perspective view of an ultrasound catheter system constructed according to the principles of the present invention.

Referring now to FIG. 1, one embodiment of an over-the-wire ultrasound catheter system 20 suitably includes an ultrasound catheter 10, a proximal end connector assembly 12 coupled with catheter 10, an ultrasound transducer 14 coupled with the proximal end of proximal connector assembly 12, and an ultrasound generator 16 with a foot-actuated on/off switch 18, which is operatively coupled with ultrasound transducer 14 to provide ultrasonic energy to transducer 14 and, thus, to ultrasound catheter 10. Generally, catheter 10 will include an ultrasound transmission member, or wire (not shown), for transmitting energy from the transducer 14 to a distal head 26 of the catheter. Proximal connector assembly 12, described more fully below, may have a Y-connector 15 with one or more side-arms 13, for example for providing irrigation fluid via an irrigation tube 11. The catheter 10 may be passed along a guide wire 17 which accesses catheter 10 via a side aperture. The side aperture may be located close to the distal end of catheter 10 or in another embodiment (not shown) close to the proximal end of catheter 10.

Ultrasound catheters 10 of the present invention may be used with any suitable combination of devices, such as any suitable ultrasound transducer 14, ultrasound generator 16, and/or the like. Therefore, exemplary FIG. 1 and any following descriptions of ultrasound catheter apparatus or systems should in no way be interpreted to limit the scope of the present invention as defined in the appended claims. Again, exemplary ultrasound catheters which may incorporate one or more improvements of the present invention are described in previously incorporated U.S. patent application Ser. No. 10/229,371. Other exemplary catheters are described in U.S. patent application Ser. No. 10/345,078, filed on Jan. 14, 2003, entitled "Ultrasound Catheter and Methods for Making and Using Same," by an inventor of the present invention, the full disclosure of which is hereby incorporated by reference. On the other hand, any suitable ultrasound catheter now known or hereafter discovered may be configured to include one or more improvements of the present invention and, thereby, fall within the scope of the present invention.

Figure 2:
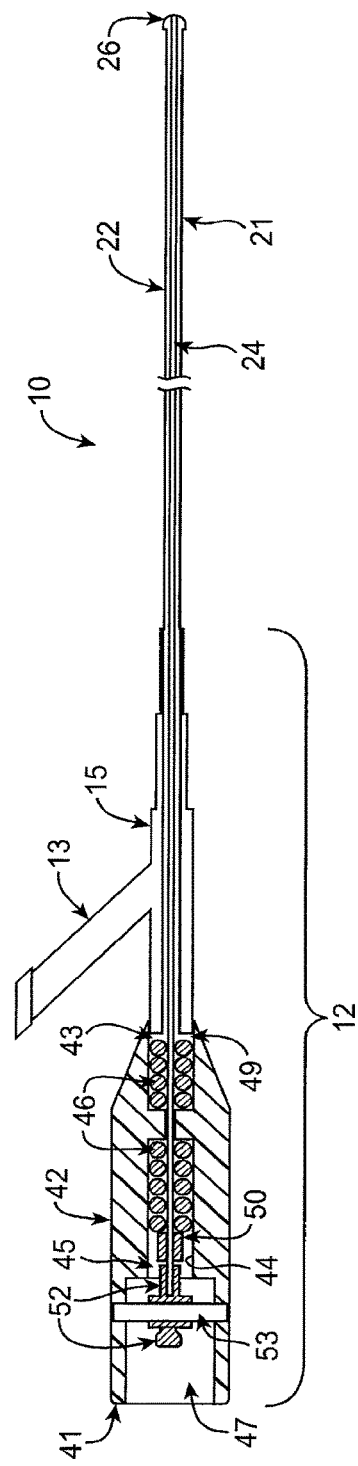
FIG. 2 is a cross-sectional view of an ultrasound catheter having an absorber member according to an embodiment of the present invention.

Referring now to FIGS. 2 and 3, cross-sectional side views of ultrasound catheter 10 and a proximal portion of ultrasound catheter 10 are shown, respectively. Generally, ultrasound catheter 10 suitably includes an elongate catheter body 22 with an ultrasound transmission member 24 disposed longitudinally through its lumen and ending in distal head 26. Catheter body 22 is generally a flexible, tubular, elongate member, having any suitable diameter and length for reaching a vascular occlusion for treatment. In one embodiment, for example, catheter body 22 preferably has an outer diameter of between about 0.5 mm and about 5.0 mm. In other embodiments, as in catheters intended for use in relatively small vessels, catheter body 22 may have an outer diameter of between about 0.25 mm and about 2.5 mm. Catheter body 22 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

In most embodiments, ultrasound transmission member 24, wire, or wave guide extends longitudinally through catheter body lumen 21 to transmit ultrasonic energy from ultrasound transducer 14, connected to the proximal end of catheter 10, to the distal end of catheter 10. Ultrasound transmission member 24 may be formed of any material capable of effectively transmitting ultrasonic energy from ultrasound transducer 14 to the distal end of catheter body 22, including but not limited to metals such as pure titanium or aluminum, or titanium or aluminum alloys.

In accordance with one aspect of the invention, all or a portion of ultrasound transmission member 24 may be formed of one or more materials which exhibit superelastic properties. Such material(s) should preferably exhibit superelasticity consistently within the range of temperatures normally encountered by ultrasound transmission member 24 during operation of ultrasound catheter apparatus 10. Specifically, all or part of the ultrasound transmission member 24 may be formed of one or more metal alloys known as "shape memory alloys."

Use of superelastic metal alloys in ultrasound transmission members is described in U.S. Pat. No. 5,267,954, previously incorporated by reference. Examples of superelastic metal alloys which may be used are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries and behavior of specific metal alloys which are superelastic within the temperature range at which the ultrasound transmission member of the present invention operates, any and all of which superelastic metal alloys may be used to form ultrasound transmission member 24 of the present invention.

In many embodiments, ultrasound transmission member 24 includes one or more tapered regions along a portion of its length, towards its distal end. Such a tapered region decreases the distal rigidity of ultrasound transmission member 24, thus amplifying ultrasound energy transmitted along ultrasound transmission member 24 to distal head 26. The tapered region typically divides the transmission member 24 between a proximal portion and a distal portion, which both typically have a larger cross-sectional diameter than the tapered region. A thicker distal portion, for example, may enhance stability of the connection between ultrasound transmission member 24 and distal head 26. Other embodiments are contemplated, however. For example, the tapered region may be positioned at the extreme distal end of transmission member 24. In still other embodiments, ultrasound transmission member 24 may include multiple tapered portions, widened portions and/or the like. Thus, ultrasound transmission member 24 may be configured with any suitable length, combinations of diameters and tapers, or any other suitable shapes, sizes or configurations to advantageously transmit ultrasound energy from transducer 14 to distal tip 26.

In some embodiments ultrasound transmission member 24 may include a low-friction coating or jacket on all or a portion of its outer surface. The coating may be disposed on the outer surface of ultrasound transmission member 24 so as to completely cover ultrasound transmission member 24 along its entire length, or along a discrete region or regions thereof. Such a coating or jacket may comprise a layer of low friction polymer material such as polytetrafluoroethylene (PTFE), TEFLON™ (available from DUPONT, INC., Wilmington, Del.) or other plastic materials such as polyethylene. The coating may be applied as a liquid and subsequently allowed to cure or harden on the surface of ultrasound transmission member 24. Alternatively, the coating may be in the form of an elongate tube, disposable over the outer surface of ultrasound transmission member 24. Generally, the coating serves to prevent or diminish friction between the outer surface of ultrasound transmission member 24 and the adjacent structures of catheter 10 or proximal end connector assembly 12 through which ultrasound transmission member 24 extends.

Figure 3A:
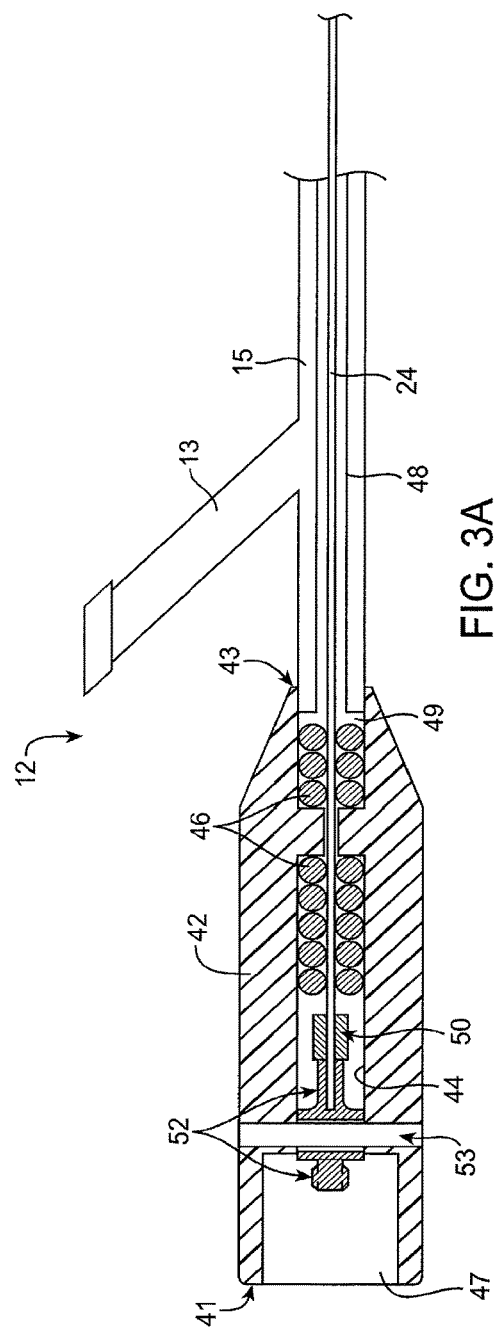
FIG. 3A is a magnified view of a proximal end of an ultrasound catheter as shown in FIG. 2.

With continued reference to FIGS. 2 and 3A, one embodiment of proximal end connector assembly 12 suitably includes a housing 42 with a hollow inner bore 44. Bore 44 may have a uniform inner diameter along its length or, alternatively, may have multiple segments, such as a proximal segment 47, a middle segment 45 and a distal segment 49, each of which may surround one or more various components of proximal end connector apparatus 12. Generally, proximal segment 47 of bore 44 is configured to allow coupling with ultrasound transducer 14 (not shown) via any suitable coupling means, such as a pressure fit, complementary threads or the like. Proximal segment 47 includes a sonic connector 52 for transmitting vibrational energy from transducer 14 to ultrasound transmission member 24. In some embodiments, sonic connector 52 may be held within housing 42, by means of dowel pin 53. In other embodiments, dowel pin 53 may not be included and sonic connector 52 may be positioned within housing 42 by other means.

Middle segment 45 of bore 44, in some embodiments, may surround a portion of sonic connector 52, while in other embodiments, sonic connector 52 may be housed only within proximal segment 47. Sonic connector 48 is coupled with the distal end of ultrasound transmission member 24 by any suitable means for transmitting ultrasound energy to transmission member 24 from transducer 14. An absorber member 50 is disposed around at least a portion of ultrasound transmission member 24 immediately distal and immediately adjacent to sonic connector 52. Absorber member 50 is described in further detail below, but generally is configured to abut sonic connector 52 to absorb heat and/or transverse vibrations from, and therefore reduce wear and tear on, ultrasound transmission member 24. Optionally, some embodiments further include one or more O-rings 46 distal to absorber member 50 and disposed about ultrasound transmission member 24 for providing further absorption of transverse vibration. Absorber member 50 and O-rings 46 may be used in any number or combination and have any suitable size and configuration, depending on the desired level of vibration absorption or dampening. Alternatively or additionally, other dampening structures may be used. Thus, the invention is not limited to the combination shown in FIG. 2.

Distal segment 49 of bore 44 typically surrounds a portion of ultrasound transmission member 24 and may also contain one or more additional sets of absorber members 46. Distal segment 49 may also contain a portion of a Y-connector 15, which is coupled with the distal end 43 of housing 42 of proximal end connector apparatus 12. Coupling of Y-connector 15 with distal end 43 of proximal end connector assembly 12 may be accomplished via complementary threads, pressure fitting, or any other suitable means. A Y-connector lumen 48 of Y-connector 15 allows passage of ultrasound transmission member 24 and is in communication with the catheter body lumen.

Generally, pressurized fluid such as a coolant liquid may be infused through side-arm 13, through Y-connector lumen 45 and through the catheter body lumen so that it flows out of one or more fluid outflow apertures in distal head. The temperature and flow rate of such coolant liquid may be specifically controlled to maintain the temperature of ultrasound transmission member 24 at a desired temperature within its optimal working range. In particular, in embodiments of the invention wherein ultrasound transmission member 24 is formed of a metal alloy which exhibits optimal physical properties (e.g. super elasticity) within a specific range of temperatures, the temperature and flow rate of coolant liquid infused through fluid infusion side-arm 13 may be specifically controlled to maintain the temperature of ultrasound transmission member 24 within a range of temperatures at which it demonstrates its most desirable physical properties. For example, in embodiments of the invention wherein ultrasound transmission member 24 is formed of a shape memory alloy which exhibits super elasticity when in its martensite state, but which loses super elasticity as it transitions to an austenite state, it will be desirable to adjust the temperature and flow rate of the coolant liquid infused through fluid infusion side-arm 13 so as to maintain the shape memory alloy of ultrasound transmission member 24 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through side-arm 13 will be at such temperature, and will be infused at such rate, as to maintain the shape memory alloy of ultrasound transmission member 24 below its martensite transition temperature.

Figure 3B:
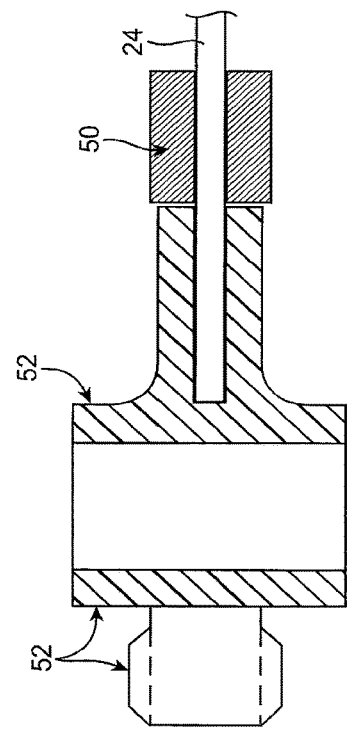
FIG. 3B is a further magnified view of a proximal end of an ultrasound catheter as shown in FIGS. 2 and 3A.

Referring to FIGS. 3A and 3B, one embodiment of absorber member 50 of the present invention is shown disposed about ultrasound transmission wire 24 and immediately adjacent the distal end of sonic connector 52. Generally, absorber member 50 may have any suitable size, shape or configuration, may be made of any suitable material, and may be coupled with ultrasound transmission member 24 by any suitable means to provide for absorption or dampening of heat, transverse vibrations, other unwanted stresses on ultrasound transmission member 24 and/or the like. Typically, absorber member 50 is made from relatively light-weight material(s), so that little or no additional load is placed on the transmission wire. In some embodiments, absorber member 50 comprises one or more materials having heat transfer properties for absorbing heat from ultrasound transmission member 24. Essentially, such an absorber member 50 acts as a heat sink to help prevent ultrasound transmission member from increasing in temperature to a level which may increase wear and tear of transmission member 24. Materials which may be used for providing absorber member with heat absorption properties, for example, may include but are not limited to aluminum and its alloys, magnesium and it alloys and/or titanium and its alloys.

Absorber member 50 may be coupled with ultrasound transmission member 24 by any suitable means. In some embodiments, for example, absorber member 50 may be positioned at a desired location on transmission member 24 during manufacturing and then may be crimped, using a crimping device, to adhere to transmission member 24. Other methods for coupling absorber member 50 with transmission member 24 are also contemplated, such as pressure fitting, use of adhesive substances, and the like.

Absorber members 50 of the present invention are generally positioned on transmission member 24 at a location adjacent to the distal end of sonic connector 52. As shown in FIG. 3A, in some embodiments absorber member 50 is positioned immediately adjacent and abutting the distal end of sonic connector 52. In other embodiments, as in FIG. 3B, absorber member 50 may be disposed very close to the distal end of sonic connector 52 without actually abutting or touching sonic connector 52. In various embodiments, for example, the distance between the distal end of sonic connector 52 and the proximal end of absorber member 50 may range up to a few millimeters.

Figure 4C:
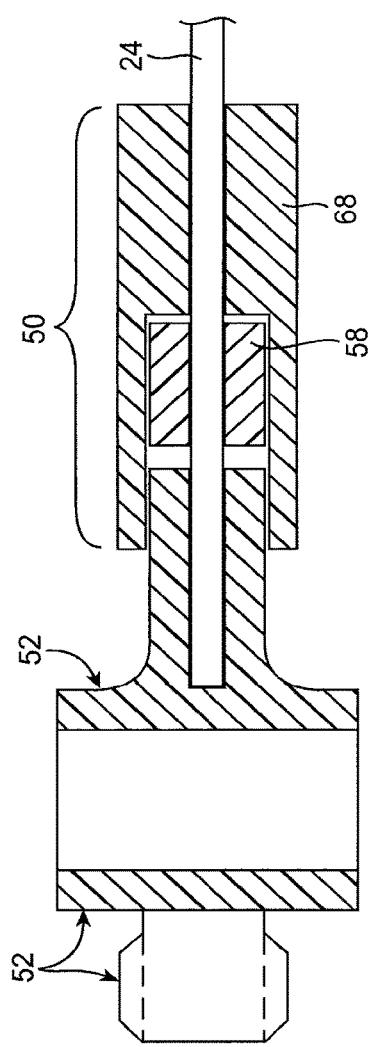

With reference now to FIGS. 4A and 4C, various embodiments of proximal end connector apparatus 12 may include an absorber member 50 having two or more component parts and/or comprising two or more different materials. For example, in some embodiments absorber member 50 includes a vibrational absorber 58 immediately surrounding transmission member 24 and a constraining member 56 immediately surrounding vibrational absorber 58. In various embodiments, vibrational absorber 58 and/or constraining member 56 may be configured to absorb transverse vibrations, absorb/transfer heat, or both. In some embodiments, for example, vibrational absorber 58 is made from a polymer or plastic capable of absorbing both vibrations and heat, while constraining member 56 is configured primarily to hold vibrational absorber 58 in place on transmission member 24.

In other embodiments, for example as in FIG. 4B, a differently shaped constraining member 64 may include one or more heat absorptive materials, and part of constraining member 64 may contact transmission member 24 or be disposed in close proximity to transmission member 24 to absorb heat generated in transmission member 24. Constraining member 64 may also absorb vibrations in some embodiments. In various embodiments, therefore, constraining member 56, 64 may serve a constraining function, a vibrational absorption function, a heat absorption function, or any combination thereof Referring now to FIG. 4C, another embodiment of absorber member 50 includes a constraining member 68 that overlaps a distal portion of sonic connector 52. Again, such a constraining member 68 may provide for vibration and/or heat absorption in addition to the constraining function. In such overlapping embodiments, vibrational absorber 58 may directly abut the distal end of sonic connector 52 or may be spaced apart from sonic connector 52, as shown in FIG. 4C. Generally, absorber members 50 of the invention will include at least one part that abuts or is closely adjacent to sonic connector 52, but may include one or more parts that are separate as well, as in FIG. 4C. As is evident from FIGS. 4A-4C, absorber member 50 may include any suitable combination of component parts having any suitable configuration and comprising any suitable combination of materials. In other embodiments, of course, absorber member 50 may comprise one, unitary piece, may comprise more than two components parts, or the like.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

The invention claimed is:

1. An ultrasound catheter comprising: a catheter body having at least one lumen; an ultrasound transmission member extending longitudinally through the catheter body lumen; a sonic connector coupled with a proximal end of the ultrasound transmission member, the sonic connector comprising a distal portion; and an absorber member coupled with the ultrasound transmission member, wherein the absorber member comprises a vibrational absorber and a constraining member, the vibrational absorber being laterally interposed between the constraining member and the ultrasound transmission member, and the vibrational absorber being longitudinally interposed along a longitudinal axis of the ultrasound transmission member between the constraining member and the distal portion of the sonic connector, and a portion of the constraining member positioned to surround an exterior of the distal portion of the sonic connector.

2. The ultrasound catheter of claim 1 wherein the vibrational absorber comprises a bore and the ultrasound transmission member extends through the bore.

3. The ultrasound catheter of claim 2 wherein the constraining member is longer than the vibrational absorber and comprises a bore with a widened portion, the vibrational absorber is disposed at least partially within the widened portion, and the transmission member extends longitudinally through the bore.

4. The ultrasound catheter of claim 3 wherein the constraining member, the vibrational absorber, or both absorb vibrations, heat, or both.

5. The ultrasound catheter of claim 4 wherein the constraining member is coupled with at least one of the vibrational absorber and the ultrasound transmission member by at least one of crimping, bonding, fusing, or welding.

6. The ultrasound catheter of claim 1 wherein the constraining member, the vibrational absorber, or both absorb vibrations, heat, or both.

7. The ultrasound catheter of claim 6 wherein the vibrational absorber comprises at least one vibration absorbing material selected from the group consisting of a rubber, a polymer, and a rubber/polymer combination.

8. The ultrasound catheter of claim 7 wherein the vibrational absorber further comprises a metal.

9. The ultrasound catheter of claim 8 wherein the metal is any one or any combination of aluminum, aluminum alloys, titanium, titanium alloys, magnesium, or magnesium alloys.

10. The ultrasound catheter of claim 1 wherein the absorber member is coupled with the ultrasound transmission member by at least one of crimping, bonding, fusing, or welding.

11. The ultrasound catheter of claim 1 wherein the absorber member is separated from the sonic connector by a distance of approximately ¼ wavelength of an ultrasound wave transmitted through the ultrasound transmission member.

12. The ultrasound catheter of claim 1 wherein the constraining member is coupled with at least one of the vibrational absorber and the ultrasound transmission member by at least one of crimping, bonding, fusing, or welding.

13. The ultrasound catheter of claim 1, wherein the vibrational absorber is disposed distally of a distal terminal end of the sonic connector.

14. The ultrasound catheter of claim 13, wherein the constraining member extends proximally and distally beyond the vibrational absorber.

15. The ultrasound catheter of claim 14, wherein the vibration absorber directly abuts a distal end of the sonic connector.

16. The ultrasound catheter of claim 14, wherein the vibrational absorber is distally spaced from a distal end of the sonic connector.

17. The ultrasound catheter of claim 14, wherein the sonic connector directly contacts the ultrasound transmission member.

18. The ultrasound catheter of claim 17, wherein the vibrational absorber directly contacts the ultrasound transmission member.

19. The ultrasound catheter of claim 18, wherein the constraining member directly contacts the ultrasound transmission member.

* * * * *